(12) United States Patent
Tajima

(10) Patent No.: US 7,608,411 B2
(45) Date of Patent: Oct. 27, 2009

(54) PROSTAGLANDIN RECEPTOR EP1

(75) Inventor: Hisao Tajima, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 149 days.

(21) Appl. No.: 11/470,213

(22) Filed: Sep. 5, 2006

(65) Prior Publication Data
US 2007/0009514 A1 Jan. 11, 2007

Related U.S. Application Data (62) Division of application No. 10/472,362, filed as application No. PCT/JP02/02757 on Mar. 22, 2002, now abandoned.

(30) Foreign Application Priority Data
Mar. 23, 2001 (JP) .......................... P.2001-085480

(51) Int. Cl.
*G01N 33/53* (2006.01)

(52) U.S. Cl. .................. 435/7.2; 435/7.21; 435/7.1; 435/69.1

(58) Field of Classification Search .................. None
See application file for complete search history.

(56) References Cited

U.S. PATENT DOCUMENTS
5,985,597 A  11/1999  Ford-Hutchinson et al.

FOREIGN PATENT DOCUMENTS
WO  WO 94/28125 A1  12/1994
WO  WO 00/29614 A1  5/2000

OTHER PUBLICATIONS
Abramowitz, Biochem. Biophys. Acta. Jan. 17, 2000;1483(2):285-293.*

* cited by examiner

*Primary Examiner*—Daniel C Gamett
(74) *Attorney, Agent, or Firm*—Sughrue Mion, PLLC

(57) ABSTRACT

(1) A novel polypeptide prostaglandin E receptor, (2) a cDNA encoding the polypeptide and a fragment selectively hybridized to the sequence of the cDNA, (3) a replication or expression vector carrying the DNA, (4) a host cell transformed with the replication or the expression vector, (5) a method for producing the polypeptide which comprises culturing the host cells, (6) a monoclonal or polyclonal antibody against the polypeptide, (7) a pharmaceutical composition containing the polypeptide or the antibody, in association with pharmaceutically acceptable excipient and/or antibody, (8) a screening method for a compound having agonistic or antagonistic activity against EP1, comprising using the polypeptide or the host cell.

The polypeptide of the present invention can be used for treating diseases, which is caused by over production of $PGE_2$, such as pain, fever and pollakiuria.

2 Claims, 3 Drawing Sheets

SEQUENCE LISTING

```
<160> NUMBER OF SEQ ID NOS: 4

<210> SEQ ID NO 1
<211> LENGTH: 402
<212> TYPE: PRT
<213> ORGANISM: Homo sapien

<400> SEQUENCE: 1

Met Ser Pro Cys Gly Pro Leu Asn Leu Ser Leu Ala Gly Glu Ala Thr
1               5                   10                  15

Thr Cys Ala Ala Pro Trp Val Pro Asn Thr Ser Ala Val Pro Pro Ser
            20                  25                  30

Gly Ala Ser Pro Ala Leu Pro Ile Phe Ser Met Thr Leu Gly Ala Val
        35                  40                  45

Ser Asn Leu Leu Ala Leu Ala Leu Leu Ala Gln Ala Ala Gly Arg Leu
    50                  55                  60

Arg Arg Arg Arg Ser Ala Ala Thr Phe Leu Leu Phe Val Ala Ser Leu
```

|   |   |   | 65  |   |   |   | 70  |   |   |   | 75  |   |   |   | 80  |
|---|---|---|---|---|---|---|---|---|---|---|---|---|---|---|---|

Leu Ala Thr Asp Leu Ala Gly His Val Ile Pro Gly Ala Leu Val Leu
                 85                      90                      95

Arg Leu Tyr Thr Ala Gly Arg Ala Pro Ala Gly Gly Ala Cys His Phe
              100                     105                     110

Leu Gly Gly Cys Met Val Phe Phe Gly Leu Cys Pro Leu Leu Leu Gly
             115                     120                     125

Cys Gly Met Ala Val Glu Arg Cys Val Gly Val Thr Arg Pro Leu Leu
      130                    135                     140

His Ala Ala Arg Val Ser Val Ala Arg Ala Arg Leu Ala Leu Ala Ala
145                  150                     155                160

Val Ala Ala Val Ala Leu Ala Val Ala Leu Leu Pro Leu Ala Arg Val
             165                     170                     175

Gly Arg Tyr Glu Leu Gln Tyr Pro Gly Thr Trp Cys Phe Ile Gly Leu
             180                     185                     190

Gly Pro Pro Gly Gly Trp Arg Gln Ala Leu Leu Ala Gly Leu Phe Ala
             195                     200                     205

Ser Leu Gly Leu Val Ala Leu Leu Ala Ala Leu Val Cys Asn Thr Leu
       210                    215                     220

Ser Gly Leu Ala Leu Leu Arg Ala Arg Trp Arg Arg Ser Arg Arg
225                  230                     235                240

Pro Pro Pro Ala Ser Gly Pro Asp Ser Arg Arg Trp Gly Ala His
             245                     250                     255

Gly Pro Arg Ser Ala Ser Ala Ser Ser Ala Ser Ser Ile Ala Ser Ala
      260                    265                     270

Ser Thr Phe Phe Gly Gly Ser Arg Ser Gly Ser Ala Arg Arg Ala
             275                     280                     285

Arg Ala His Asp Val Glu Met Val Gly Gln Leu Val Gly Ile Met Val
      290                    295                     300

Val Ser Cys Ile Cys Trp Ser Pro Met Leu Val Leu Val Ala Leu Ala
305                  310                     315                320

Val Gly Gly Trp Ser Ser Thr Ser Leu Gln Arg Pro Leu Phe Leu Ala
             325                     330                     335

Val Arg Leu Ala Ser Trp Asn Gln Ile Leu Asp Pro Trp Val Tyr Ile
             340                     345                     350

Leu Leu Arg Gln Ala Val Leu Arg Gln Leu Leu Arg Leu Leu Pro Pro
         355                    360                    365

Arg Ala Gly Ala Lys Gly Gly Pro Ala Gly Leu Gly Leu Thr Pro Ser
      370                    375                     380

Ala Trp Glu Ala Ser Ser Leu Arg Ser Ser Arg His Ser Gly Leu Ser
385                  390                     395                400

His Phe

<210> SEQ ID NO 2
<211> LENGTH: 1209
<212> TYPE: DNA
<213> ORGANISM: Homo sapien
<220> FEATURE:
<221> NAME/KEY: protein_bind
<222> LOCATION: (1)..(1209)

<400> SEQUENCE: 2
atgagccctt gcgggcccct caacctgagc ctggcgggcg aggcgaccac atgcgcggcg    60 ccctgggtcc ccaacacgtc ggccgtgccg ccgtcgggcg cttcgccgcc gctgcccatc   120

-continued

```
ttctccatga cgctgggcgc cgtgtccaac ctgctggcgc tggcgctgct ggcgcaggcc      180
gcgggccgcc tgcgacgccg ccgctcggcc gccaccttcc tgctgttcgt ggccagcctg      240
ctggccaccg acctggcggg ccacgtgatc ccgggcgcgc tggtgctgcg tctgtacact      300
gcggggcgcg ctccggccgg cggggcctgc cacttcctgg gcggctgcat ggtcttcttc      360
ggcctgtgcc cgctgctgct gggctgtggc atggccgtgg agcgctgcgt gggcgtcacg      420
cggccgctgc tccacgccgc gcgggtctcg gtcgcccgcg cgcgcctggc gctggccgcg      480
gtggccgcgg tggccttggc cgtggcgctg ctgccgctgg cgcgcgtggg ccgctatgag      540
ctgcagtacc cgggcacgtg gtgcttcatc ggcctgggtc cccgggcgg ctggcgccag       600 gcactgcttg ctggcctctt cgccagcctc ggcctggtcg cgctcctcgc cgcgctggtg      660
tgcaacacgc tcagcggcct ggccctgcta cgcgcccgct ggcgacgccg ctcccgacgg      720
cctcccccgg cctcaggccc cgacagccgg cgtcgctggg gggcgcacgg accccgctcg      780
gcctccgcct cgtccgcctc gtccatcgct tcggcctcca ccttctttgg cggctctcgg      840
agcagcggct cggcacgcag agctcgcgcc cacgacgtgg agatggtggg ccagcttgtc      900
ggtatcatgg tggtgtcgtg catctgctgg agcccaatgc tggtgttggt ggcgctggcc      960
gtcggcggct ggagctctac ctccctgcag cggccactat tcctggccgt gcgccttgcc     1020
tcctggaacc agatcctgga cccttgggtg tacatcctac tgcgccaggc cgtgctgcgc     1080
caactgcttc gcctcttgcc cccgagggcc ggagccaagg gcggccccgc ggggctgggc     1140
ctaacaccga gcgcctggga ggccagctcg ctgcgcagct cccggcacag cggcctcagc     1200
cacttctaa                                                            1209
```

<210> SEQ ID NO 3
<211> LENGTH: 21
<212> TYPE: DNA
<213> ORGANISM: Artificial Sequence
<220> FEATURE:
<223> OTHER INFORMATION: Forward primer

<400> SEQUENCE: 3
tggcgcctga catgagccct t                                                 21

<210> SEQ ID NO 4
<211> LENGTH: 24
<212> TYPE: DNA
<213> ORGANISM: Artificial Sequence
<220> FEATURE:
<223> OTHER INFORMATION: Reverse primer

<400> SEQUENCE: 4
tcgttgggcc tctggttgtg ctta                                              24

PROSTAGLANDIN RECEPTOR EP1

TECHNICAL FIELD OF THE INVENTION

This is a divisional of application Ser. No. 10/472,362 filed Sep. 23, 2003 now abandoned, which is a 371 National Stage application of PCT/JP02/02757, filed Mar. 22, 2002. The entire disclosure(s) of the prior application(s), application Ser. Nos. 10/472,362 and PCT/JP02/02757 is/are hereby incorporated by reference.

The present invention relates to a novel polypeptide prostaglandin E (hereinafter, simply referred to as "PGE") receptor.

In more detail, the present invention relates to (1) a novel polypeptide, (2) a cDNA encoding the polypeptide and a fragment selectively hybridized to the sequence of the cDNA, (3) a replication or expression vector carrying the DNA, (4) a host cell transformed with the replication or the expression vector, (5) a method for producing the polypeptide which comprises culturing the host cells, (6) a monoclonal or polyclonal antibody against the polypeptide, (7) a pharmaceutical composition containing the polypeptide or the antibody, in association with pharmaceutically acceptable excipient and/or antibody, (8) a screening method for a compound having agonistic or antagonistic activity against EP1, comprising using the polypeptide, and (9) a screening method for a compound having agonistic or antagonistic activity against EP1, comprising using the host cells.

BACKGROUND OF THE INVENTION

Prostanoids such as prostaglandin (PG), thromboxane (TX) and leukotriene (LT) are the family of oxidized metabolites of arachidonic acid, and demonstrate various physiological actions for maintaining local homeostasis in the living body (The Pharmacological Basis of Therapeutics (Gilman, A. G., Goodman, L. S., Rall, T. W., and Murad, F., eds) 7th Ed., pp 660, Macmillan Publishing Co., New York (1985)). Their physiological actions are regulated through a membrane-bound receptor specific for each prostanoid (Annu. Rev. Pharm. Tox., 10, 213 (1989) Prostanoids and their Receptors. In Comprehensive Medicinal Chemistry., pp 643 (1990), Pergamon Press, Oxford). Prostaglandin E (PGE), a member of prostanoids, especially prostaglandin $E_2$ ($PGE_2$) participates widely in contraction and relaxation of gastrointestinal tract, secretion of gastric acid, relaxation of smooth muscle, and release of neurotransmitters. Based on the results obtained by the analysis of physiological and pharmacological actions of PGE2 and its site of action, it is thought that there are 4 subtype receptors including EP1, EP2, EP3 and EP4 (Negishi M. et al, J. Lipid Mediators Cell Signalling, 12, 379-391 (1995)) and that each receptor is involved in a different signal transduction.

Among them, it is known that EP1 is involved in pain, fever and diuresis (Br. J. Pharmacol., 1994, 112, 735-40, European J. Pharmacol., 152 (1988) 273-279, Gen Pharmacol., September 1992, 23(5) p805-809). Therefore, it is thought that antagonizing the receptor may be effective for treating pain, fever and pollakiuria. To clarify these points, it is essential to analyze a structure of EP1 receptor, a signaling and tissue distribution of the receptor.

The amino acid sequence of EP1 receptor (Accession No. AAC37539.1) and the nucleotide sequence encoding it (Accession No. L22647) are disclosed in Japanese Patent No. 3,090,472. However, detailed comparison of the sequences with those of human EP1 receptor of the present invention revealed that there are 4 discrepancies in nucleotide sequence and 2 in amino acid sequence, respectively.

The amino acid sequence of the polypeptide of the present invention was searched against the SwissProt amino acid sequence databases (Swiss Prot Release2.0), there was no identical sequence that corresponded to the polypeptide. The nucleotide sequence of the DNA encoding the polypeptide of the present invention was also searched against the GenBank nucleotide sequence databases (GenBank Release70.0), no identical sequence that corresponded to the DNA was found. Accordingly, it was confirmed that the polypeptide of the present invention was a novel one.

DISCLOSURE OF THE INVENTION

The inventors of the present invention have successfully cloned a cDNA of human EP1 receptor, expressed it in mammalian cells, demonstrated that it encoded human EP1 receptor, and thus completed the present invention.

Furthermore, as shown in examples bellow, the extremely high specific binding of [$^3$H]-$PGE_2$ to the receptor and the $PGE_2$ dependent elevation of intracellular $Ca^{2+}$ concentration were seen in the cells expressed with the human EP1 receptor of the present invention. In contrast, it has become clear that the specific binding of [$^3$H]-$PGE_2$ to the receptor but no $PGE_2$ dependent elevation of intracellular $Ca^{2+}$ concentration were seen in the cells expressed with the human EP1 receptor which is disclosed in Japanese Patent No. 3,090,472.

The present invention relates to (1) a polypeptide comprising the amino-acid sequence shown in SEQ ID NO:1, (2) a cDNA encoding the polypeptide according to (1), (3) a DNA according to (2), comprising the nucleotide sequence shown in SEQ ID NO:2, or a fragment DNA selectively hybridized to the sequence, (4) a replication or expression vector carrying the DNA according to (2) or (3), (5) a host cell transformed with the replication or the expression vector according to (4), (6) a method for producing the polypeptide according to (1) which comprises culturing the host cells according to (5) under a condition effective to express the polypeptide according to (1), (7) a monoclonal or polyclonal antibody against the polypeptide according to (1), (8) a pharmaceutical composition containing the polypeptide according to (1) or the antibody according to (7), in association with pharmaceutically acceptable excipient and/or antibody, (9) a screening method for a compound having agonistic or antagonistic activity against EP1, comprising using the polypeptide according to (1), and (10) a screening method for a compound having agonistic or antagonistic activity against EP1, comprising using the host cells according to (5).

DETAILED DESCRIPTION OF THE INVENTION

A DNA selectively hybridizing to the nucleotide sequence shown in SEQ ID NO:2 is generally at least 70%, preferably at least 80 or 90% and more preferably at least 95% homologous to the DNA over a region of at least 100, preferably at least 150, for example 200, 250 or 300 contiguous nucleotides. Such a DNA homologue is referred to as a DNA of the present invention.

The selectively hybridizing DNAs contain complementary sequences against above sequence. The hybridization on stringent condition is preferred.

Generally, a fragment of DNA comprising nucleotide sequence shown in SEQ ID NO:2 is at least 10, preferably at least 15, for example 20, 25, 30 or 40 nucleotides in length, and is also referred to as a DNA of the present invention.

The DNA of the present invention can he obtained by recombinant DNA technologies, chemical synthesis, or methods known by a man skilled in the art.

A further embodiment of the present invention provides replication or expression vectors carrying the DNA of the present invention. The vectors may be, for example, plasmid, virus or phage vectors provided with an origin of replication, optionally a promoter for the expression of the DNA and a regulator of the promoter. The vector may contain one or more selectable marker genes, for example an ampicillin resistance gene.

A further embodiment of the present invention provides host cells transformed with the replication or expression vector carrying the DNA of the present invention, including the DNA of which nucleotide sequence is shown in SEQ ID NO:2. The cells can be for example bacterial, yeast, insect or mammalian cells.

A further embodiment of the present invention provides a method for producing the polypeptide, which comprises culturing host cells of the present invention, under conditions effective to express the polypeptide of the present invention.

As a polypeptide of the present invention, those which have deficiency in a part of the amino acid sequence shown in SEQ ID NO:1 (e.g., a polypeptide comprised of the only essential sequence for revealing a biological activity in their mature amino acid sequence), those which have a part of their amino acid sequence replaced by other amino acids (e.g., those replaced by an amino acid having a similar property) and those which have other amino acids added or inserted into a part of their amino acid sequence, as well as those comprising the amino acid sequence shown in SEQ ID NO:1, are provided.

As known well, there are one to six kinds of codon encoding one amino acid (for example, one kind of codon for Methionine (Met), and six kinds of codon for leucine (Leu) are known). Accordingly, the nucleotide sequence of a DNA can be changed without changing the amino acid sequence of a polypeptide.

The DNA of the present invention according to (2) includes every group of nucleotide sequences encoding polypeptide shown in SEQ ID NO:1. There is a probability that yield of a polypeptide is improved by changing a nucleotide sequence.

The DNA specified in SEQ ID NO:2 according to (3) is one embodiment of the DNA according to (2), and indicates the sequence of natural form.

The DNA having the nucleotide sequence shown in SEQ ID NO:2 is prepared by the following methods:

That is:
(i) Them RNA is prepared from cells that produce the polypeptide of the present invention,
(ii) The first-strand DNA (a single-strand DNA) is synthesized by using the mRNA as a template, then the second-strand DNA (a double-strand DNA) is synthesized (preparation of DNA),
(iii) The DNA fragment is inserted into an appropriate plasmid vector,
(iv) Host cells are transformed with the recombinant vectors (preparation of cDNA library),
(v) The plasmid containing the aimed DNA is isolated from the cDNA library by using hybridization method, and
(vi) The aimed DNA is prepared by sequencing the DNA insert of the plasmid.

Detailed description of each step is as follows:

In step (i), mRNA is isolated from human organ that expresses EP1 receptor, preferably from tissue or cell line such as brain, placenta, neuroblastoma (T98G etc.), and erythro-leukemia (Hel etc.), by the method of Okayama, H et al. (Method in Enzymology 154, 3 (1987)) or Chirgwin, J. M. et al. (Biochem. 18, 5294 (1979)).

In steps (ii), (iii) and (iv), a cDNA library is prepared by the modified method of Gubler & Hoffman (Gene 25, 263 (1983)). For plasmid vector to be used in step (iii), various vectors, which is functional in *E. coli* (for example pBR322) or in *B. subtilis* (for example pUB110), are known. Preferably λ-ZAPII that is functional in *E. coli* is used. In step (iv), a host cell can be chosen from a variety of host cells known, preferably competent cells (prepared by the method described in Gene 96, 23 (1990)) of *E. coli* strain DH5 is used.

Recently, cDNA libraries prepared from a variety of tissues of animals, which are already on the market, can also be used preferably.

In step (v), hybridization is carried out by the known methods such as plaque hybridization or colony hybridization (Gene 10, 63 (1980)) etc. As a probe, a DNA of EP1 receptor from another animal than human, a fragment thereof, or a DNA homologous to said DNA could be used.

In step (vi), sequencing can be performed by the known method such as the method of dideoxy terminator or the method of Maxam-Gilbert.

Once the nucleotide sequence shown in SEQ ID NO:2 is identified, then the DNA of the present invention can be obtained by chemical synthesis, PCR method, or hybridization method by using the fragment of said nucleotide sequence as a probe. Furthermore, a necessary amount of the DNA of the present invention can be obtained by introducing a vector containing the DNA to an appropriate host cell, followed by proliferating the cells.

The polypeptides of the present invention (SEQ ID NO:1) may be prepared by:
(1) isolating and purifying from an organism or a cultured cell,
(2) chemically synthesizing, or
(3) using recombinant DNA technology, preferably, by the method described in (3) in an industrial production.

Examples of expression system (host-vector system) for producing a polypeptide by using recombinant DNA technology are the expression systems of bacteria, yeast, insect cells and mammalian cells.

In the expression of the polypeptide, for example, in *E. Coli*, the expression vector is prepared by connecting the DNA encoding mature protein (for example the DNA shown in SEQ ID NO:2) to the downstream of a proper promoter (e.g., trp promoter, lac promoter, λ PL promoter, and T7 promoter), and then inserting it into a vector (e.g., pBR322, pUC18 and pUC19) which functions in an *E. coli* strain. Then, an *E. coli* strain (e.g., *E. coli* strain DH1, *E. coli* strain JM109 and *E. coli* strain HB101) which is transformed with the expression vector described above may be cultured in an appropriate medium to obtain the desired polypeptide. When a signal peptide of bacteria (e.g., signal peptide of pel B) is utilized, the desired polypeptide may be also released in periplasm. Furthermore, a fusion protein with other polypeptide may be also produced easily.

In the expression of the polypeptide, for example, in mammalian cells, for example, the expression vector is prepared by inserting the DNA encoding the nucleotide sequence shown in SEQ ID NO:2 into the downstream of a proper promoter (e.g., SV40 promoter, LTR promoter and metallothionein promoter) in a proper vector (e.g., vaccinia virus vector and SV40 vector) A proper mammalian cell (e.g., monkey COS-7 cell, Chinese hamster CHO cell, mouse L cell etc.) is transfected with the expression vector thus obtained, and then the transfectant is cultured in a proper medium, the aimed polypeptide can be secreted into the culture medium. The polypeptides thus obtained can be isolated and purified by conventional biochemical methods.

The present invention also provides monoclonal or polyclonal antibodies against the polypeptide of the present invention. The present invention further provides a process for production of monoclonal or polyclonal antibodies against the polypeptide of the present invention. Monoclonal antibodies can be prepared by common hybridoma technology using the polypeptide of the present invention or fragments there of as an immunogen. Polyclonal antibodies can also be prepared by common means which comprises inoculating host animals (for example rat or rabbit) with the polypeptide of the present invention and recovering the immune serum.

The present invention also provides pharmaceutical compositions containing a polypeptide of the present invention, or an antibody thereof, in association with a pharmaceutically acceptable excipient and/or carrier.

The DNA of the present invention may also be inserted into the vectors described above in an antisense orientation in order to produce antisense RNA. Such antisense RNA may be used in controlling the level of the polypeptide of the present invention in a cell.

ADMINISTRATION AND DOSING

For treating diseases such as pain, fever and pollakiuria, administration of the polypeptide of the present invention or its antibodies can be carried out in systemic or local, generally peroral or parenteral ways. Oral, intravenous and intracerebroventricular administrations are preferred.

The dosage to be administered depends upon age, body weight, symptom, desired therapeutic effect, route of administration, and duration of the treatment etc. In human adults, one dose per person is generally between 100 μg and 100 mg by oral administration up to several times per day, and between 10 μg and 100 mg by parenteral administration up to several times per day.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, as injections, liniments or suppositories etc. for parenteral administration.

Examples of solid compositions for oral administration include compressed tablets, pills, capsules, dispersible powders and granules. Examples of capsules include soft capsules and hard ones.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.).

The tablets or pills may, if desired, be coated with a film of gastric or enteric materials such as sugar, gelatin, hydroxypropyl cellulose or hydroxypropylmethyl cellulose phthalate, or be coated with more than two films. And then, coating may include containment within capsules of absorbable materials such as gelatin.

Liquid compositions for oral administration may contain pharmaceutically acceptable emulsions, solutions, suspensions, syrups and elixirs, and also may contain inert diluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active substance(s). Spray compositions may comprise additional substances other than inert diluents: e.g. stabilizing agents (sodium sulfite etc.), isotonic buffer (sodium chloride, sodium citrate citric acid, etc.). For preparation of such spray compositions, for example, the method is described in the U.S. Pat. Nos. 2,868, 691 and 3,095,355 (herein incorporated in their entireties by reference) may be used.

Injections for parenteral administration include sterile aqueous or non-aqueous solutions, suspensions and emulsions. In such compositions, one or more active compound(s) is or are admixed with at least one inert aqueous diluent (s) (distilled water for injection, physiological salt solution, etc.) or inert non-aqueous diluents(s)(propylene glycol, polyethylene glycol, olive oil, ethanol, POLYSOLBATE 80™, etc.).

Injections may comprise additional compound other than inert diluents: e.g. preserving agents, wetting agents, emulsifying agents, dispersing agents, stabilizing agent (such as human serum albumin, lactose, etc.), and assisting agents such as assisting agents for dissolving (arginine, asparaginic acid, etc.).

INDUSTRIAL APPLICABILITY

Since the polypeptide of the present invention specifically bound $PGE_2$, the polypeptide can be used for treating diseases, which is caused by over production of $PGE_2$, such as pain, fever and pollakiuria. The polypeptide may also be used for screening substances having agonistic or antagonistic activities against EP1 receptor.

Quantitative analysis of the polypeptide of the present invention in the body can be performed using polyclonal or monoclonal antibodies against the polypeptide, and thus can be used in studies on relationship between the polypeptide and diseases, or diagnosis of diseases, etc.

DETAILED DESCRIPTION OF PREFERRED EMBODIMENTS

The invention is illustrated by the following examples, but not limit the invention.

EXAMPLE 1 cDNA Cloning of Human EP1 Receptor

Erythroleukemia cell line, HEL cells were cultured and mRNA was prepared from the cells by the conventional method. RT-PCR (reverse transcrived polymerase chain reaction) was carried out in two steps with the mRNA thus obtained. After the synthesis of first strand DNA by reverse transcription, the following reaction mixture was prepared.

Reaction mixture: HEL cDNAs (1 µl), primer 1 (0.5 µM), primer 2 (0.5 µM), PCR buffer (Tris-HCl (pH8.3, 10 mM), KCl (50 mM), MgCl2 (1.5 mM)), dNTPs (mixtures of each 0.25 mM of dATP, dCTP, dGTP and dTTP), Taq polymerase (0.5 unit 1) and 10% DMSO.

```
Primer 1:
5'-TGGCGCCTGA CATGAGCCCT T-3'        (SEQ ID NO:3)

Primer 2:
5'-TCGTTGGGCC TCTGGTTGTG CTTA-3'     (SEQ ID NO:4)
```

The conditions of PCR were as follows;

First step: [(94° C., 1 min.), (62° C., 2 min.), and (72° C., 3 min.)]×25 cycles, Second step: [(94° C., 1 min.), (55° C., 2 min.), and (72° C., 3 min.)]×25 cycles.

The PCR product was subjected to agarose gel electrophoresis, the 1250-bp band having the aimed length was obtained. The band was purified, inserted into pT7 Bleu T-Vector (Novagen) (hereinafter, simply referred to as "pT7 Bleu hEP1"), and sequenced by cycle-sequencing method using fluorescence-dye terminator of ABI (Applied Biosystems Inc.) which is based upon the di-deoxynucleotide chain termination method of Sanger F. et al. DNA sequencer purchased from ABI was used for reading the nucleotide sequence. The nucleotide sequence of the cDNA encoding hEP1 receptor was shown in SEQ ID NO:2, and the deduced amino acid sequence in SEQ ID NO:1.

The nucleotide sequence of the hEP1 receptor of the present invention and the predicted amino acid sequence there of were compared with those of the hEP1 receptor described in Japanese Patent No. 3,090,472 (hereinafter, a number written on right shoulder of a nucleotide or an amino acid shows a position from "A" of ATG, translation initiation codon, and a position from "Met" that is translation initiation amino acid, respectively).

$G^{211}$ in the nucleotide sequence of the present invention was substituted by "A" in that of Japanese Patent No. 3,090,472. Hereinafter, it is shown as "$G^{211} \rightarrow A$". Similar substitutions were also found in $T^{689} \rightarrow A$, $A^{690} \rightarrow T$ and $A^{999} \rightarrow G$, thus there were 4 differences in the nucleotide sequences between them. Based upon these differences, it was found that there were 2 differences in amino acid sequences between them, i.e., $Ala^{71} \rightarrow Thr$ and $Leu^{230} \rightarrow His$.

EXAMPLE 2

Binding Assays with the Cells Expressing Human EP1 Receptor

1) Gene Transfection into CHO Cells and Isolation of Clones Expressing Human EP1 Receptor The cDNA insert was cut off from pT7BluehEP1 by EcoR1 digestion, and inserted into EcoR1 site of expression vector pdKCR-dhfr in the proper orientation. Approximately 25-50 ug of expression plasmid was digested completely with proper restriction enzymes (SalI, SacII etc.), purified by Phenol/CIAA extraction, CIAA extraction and ethanol precipitation, and dissolved in 50 µl of sterilized water. CHO-dhfr(−) cells used as host were suspended in $1.0$-$1.5 \times 10^6$ cells/0.8 ml of PBSuc buffer (sucrose 272 mM, $K^+PO_4^{2-}$ buffer (7 mM, pH7.4) and $MgCl_2$ (1 mM)). Ten microliter of Plasmid DNA and 0.8 ml of cell suspension were added into Gene Pulser Cuvette (Bio-rad, Cat. No. 165-2088), incubated for 10 minutes on ice, and pulsed with 25 uF 200-500V using Gene Pulser (Bio-rad). After additional 10 minutes incubation on ice, cells were suspended in 10 ml of medium (permissive medium; α-MEM (Dainippon Pharmaceutical Co., Ltd.) containing 100×HT supplement (GIBCO BRL), penicillin (100 U/ml), streptomycin (100 ug/ml) and 10% dialyzed FCS (GIBCO)), transferred into culture flask (75 cm²), and cultured for approximately 48 hours in $CO_2$ incubator. The cells were harvested after trypsin treatment, suspended in selection medium (non permissive medium; (α-MEM (Dainippon Pharmaceutical Co., Ltd.) containing penicillin (100 U/ml), streptmycin (100 ug/ml) and 10% dialyzed FCS (GIBCO)), and cultured.

To isolate a single colony, after several days to one-week cultivation, when colonies (20-30 cells/colony) were grown well, colonies were isolated as follows. The culture medium was removed from flasks, and cells were washed with PBS. A filter paper, which was cut into approximately 5 mm×5 mm, autoclaved and soaked in trypsin solution, was added onto each colony and incubated at 37° C. for 3 minutes. Each colony was removed from the flask with the filter paper, transferred into 24-well plate, and 1 ml/well of selection medium was added. After additional cultivation, the promising clones were selected based on a form, multiplication ability, etc. of a cell.

Alternatively, the limited dilution method was carried out. After approximately one-week cultivation, in due course when cells were growing well, cells were harvested and inoculated into several 96-well plates at 2-5 cells/well. The promising clones were selected based on a form, multiplication ability, etc. of a cell, and transferred into 24-well plate.

2) Preparation of Membrane Fraction

The CHO cloned cells expressing human EP1 receptor obtained by the above method were cultured and membrane fraction was prepared by the following methods.

The cells were cultured in large scale using 500 cm² trey (Sumitomo Bakelite Co., Ltd.) with α-MEM (Dainippon Pharmaceutical Co., Ltd.) containing penicilin (100 U/ml), streptmycin (100 ug/ml) and 10% dialyzed FCS (GIBCO). The cells were washed with PBS(−), recovered using cell-scraper, centrifuged at 1,000 rpm for 3 minutes, and the cell pellets were stored at −80° C.

The following operations for preparing cell membranes were performed at 4° C. or below. The cell pellets, which were harvested from 50-150 treys, were added with 10-fold volume of buffer A cooled on ice, and homogenized using Potter homogenizer (1,000 rpm, 5 strokes). After centrifugation at 1,000×g for 10 minutes, the lysate was centrifuged further at 100,000×g for 15 minutes. The pellets thus obtained were suspended in buffer B and stored at −80° C. as a membrane fraction until use.

Buffer A:
Tris-HCl (20 mM, pH7.5) containing EDTA (1 mM), $MgCl_2$ (10 mM), PMSF (0.1 mM), pepstatin A (10 μM) and indomethacin (20 μM);

Buffer B:
KPi (pH6.0, 10 mM) containing EDTA (1 mM), $MgCl_2$ (10M) and NaCl (0.1M).

3) Binding Assays

Reaction mixtures (200 μl) containing the membrane fraction, which was prepared by the above method and contains human EP1 receptor, and various concentrations of [3H]-$PGE_2$ were incubated at room temperature for a certain time, separated by rapid filtration using Cell Harvester (Brandel). The membrane fraction was recovered on glass filter and washed several times with the buffer cooled on ice (1-2 ml/wash). Residual [3H]-$PGE_2$ bound to the filter (total binding) was quantitated by liquid scintillation counter. Nonspecific binding was quantitated in a similar manner in the presence of 10 μM of $PGE_2$. Specific binding was defined as the difference between total binding and nonspecific binding.

Figure 1:
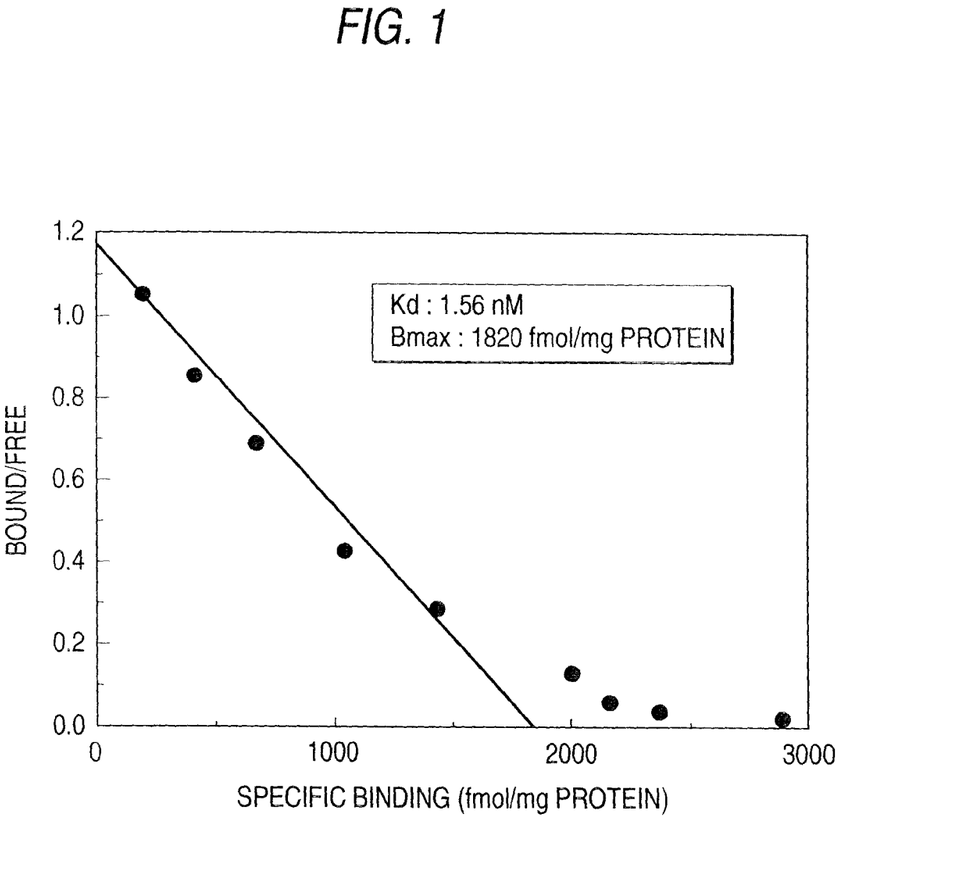
FIG. 1 shows a scatchard blot in binding assays using cells expressing human EP1 receptor of the present invention.
Figure 2:
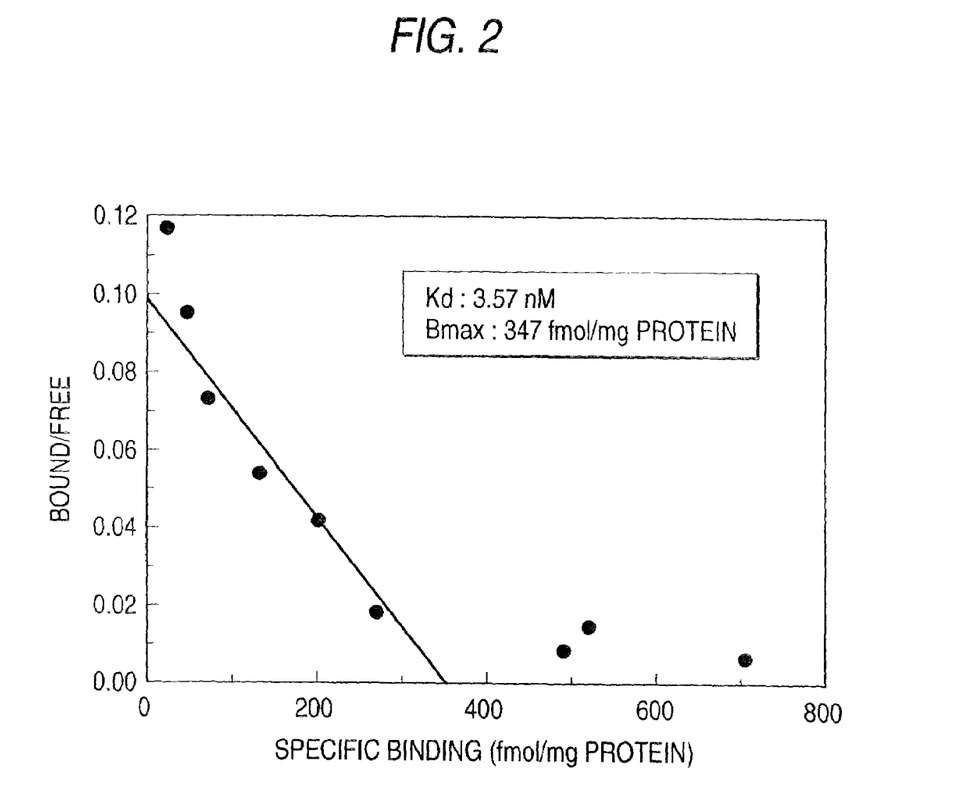
FIG. 2 shows a scatchard blot in binding assays using cells expressing human EP1 receptor described in Japanese Patent No. 3,090,472.

The specific binding thus obtained was analyzed by Scatchard plots, an equilibrium dissociation constant (Kd; nM) and a maximum number of specific binding sites (Bmax; fmol/mg protein) were determined. The result obtained using the cells expressing human EP1 of the present invention was shown in FIG. 1, and the result obtained using the cells expressing human EP1 described in Japanese Patent No. 3,090,472 in FIG. 2, respectively. The amount of hEP1 mRNA in the cells expressing human EP1 receptor used in FIGS. 1 and 2 was analyzed by quantitative PCR, no difference was found, suggesting the human EP1 receptor were expressed on both cells in equal level.

EXAMPLE 3

Measurement of Intracellular $Ca^{2+}$ Concentration in Cells Expressing Human EP1 Receptor The cells were cultured in 500 $cm^2$ treys to reach confluence, washed with PBS(−), and peeled off by pipeting with PBS(−) on ice. After centrifugation at 800 rpm for 3 minutes, the cell pellet was suspended in medium A (15 ml) and incubated at 37° C. for 50 minutes followed by at room temperature for 10 minutes. After re-centrifugation the pellet was suspended in medium B (1-2×10⁶/ml) and used for experiments. In the case that cell suspension contains Fura2-AM (Dojin), the operations were shielded the light by aluminum foil. Stirring the cell suspensions (400 μl) at 600 rpm, the changes of intracellular $Ca^{2+}$ concentration were measured by monitoring the changes of fluorescence intensity at both 340 nm and 380 nm and the ratio thereof, using CAM-220 Spectrofluorometer (Nihon Bunko Kogyo).

Medium A:
α-MEM containing fura2-AM (5 μM)), indomethacin (10 μM), HEPES-NaOH (pH7.4, 10 mM) and 10% FCS, Medium B:
α-MEM containing indomethacin (1 μM), HEPES-NaOH (pH7.4, 10 mM) and 0.1% BSA.

Figure 3:
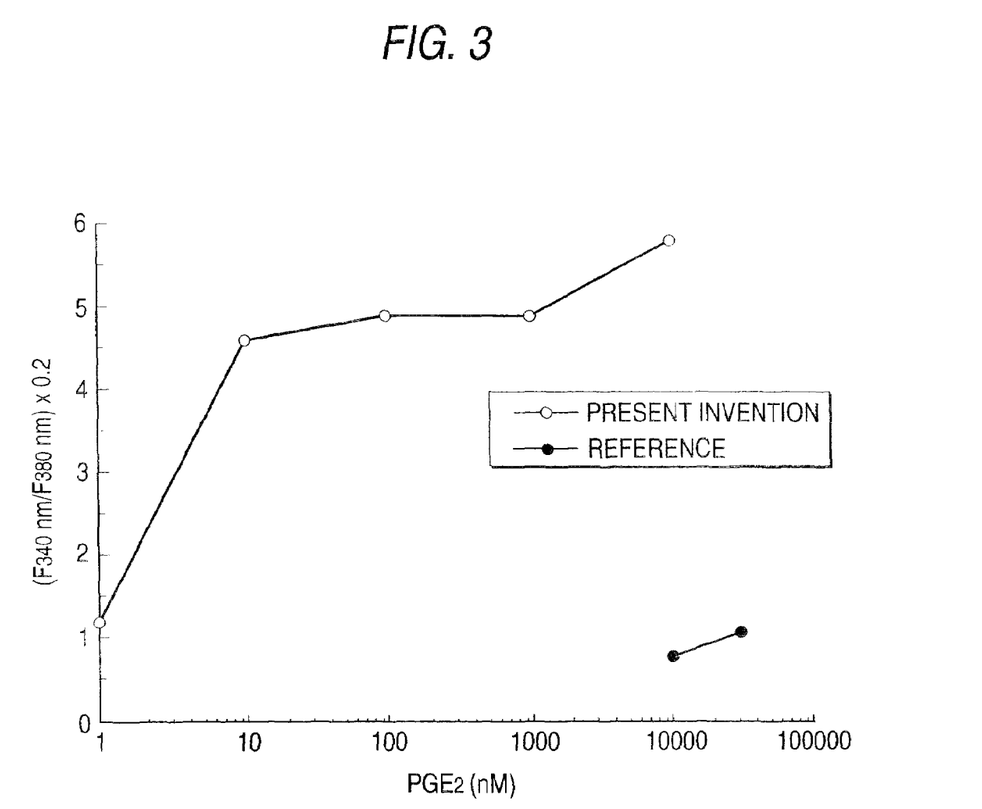
FIG. 3 shows changes of intracellular $Ca^{2+}$ concentration in the experiments using cells expressing human EP1 receptor of the present invention or that of Japanese Patent No. 3,090, 472.

The changes in intracellular $Ca^{2+}$ concentration using the cells expressing human EP1 receptor of the present invention and the cells expressing human EP1 receptor described in Japanese Patent No. 3,090,472 were shown in FIG. 3. In FIG. 3, "reference" means the result obtained by using the cells expressing human EP1 receptor described in Japanese Patent No. 3,090,472.

As obvious from examples 2 and 3, the extremely high specific binding of [³H]-$PGE_2$ to the receptor and the $PGE_2$ dependent elevation of intracellular $Ca^{2+}$ concentration were detected in the cells expressing human EP1 receptor of the present invention.

In contrast, the specific binding of [³H]-$PGE_2$ to the receptor was detected, however, the $PGE_2$ dependent elevation of intracellular $Ca^{2+}$ concentration was not detected at all in the cells expressing human EP1 receptor described in Japanese Patent No. 3,090,472.

The invention claimed is:

1. A method for screening a compound for antagonistic activity against EP1, comprising the steps of:
 (1) contacting a test compound with a cell expressing a polypeptide comprising the amino acid sequence of SEQ ID NO: 1 in the presence of at least 10 nM of $PGE_2$;
 (2) detecting intracellular $Ca^{2+}$ concentration in the cell expressing said polypeptide in the presence and absence of said test compound,
wherein when the intracellular $Ca^{2+}$ concentration in the presence of said test compound is reduced relative to the intracellular $Ca^{2+}$ concentration in the absence of said test compound, said test compound is an antagonist of EP1.

2. The method according to claim 1, wherein said cell is transformed with a replication or expression vector comprising the nucleotide sequence of SEQ ID NO: 2.

* * * * *